United States Patent
Robbins (10) Patent No.: US 7,799,292 B2
(45) Date of Patent: Sep. 21, 2010

(54) SYSTEM FOR PRODUCING CHEMICAL COMPOUNDS VIA A BARIC ELECTROMAGNETIC THERMAL PROCESS

(75) Inventor: Gregory C. Robbins, Baton Rouge, LA (US)

(73) Assignee: Quantum Food Design, LLC., Coral Gables, FL (US)

( * ) Notice: Subject to any disclaimer, the term of this patent is extended or adjusted under 35 U.S.C. 154(b) by 735 days.

(21) Appl. No.: 11/520,485

(22) Filed: Sep. 13, 2006

(65) Prior Publication Data
US 2007/0065553 A1 Mar. 22, 2007

Related U.S. Application Data

(60) Provisional application No. 60/716,803, filed on Sep. 13, 2005.

(51) Int. Cl.
| | | |
|---|---|---|
| B01J 19/00 | (2006.01) | |
| B01J 19/12 | (2006.01) | |
| B01J 3/00 | (2006.01) | |

(52) U.S. Cl. .................. 422/189; 422/198; 422/238; 422/242; 422/108; 422/186.01
(58) Field of Classification Search .................. None
See application file for complete search history.

(56) References Cited

U.S. PATENT DOCUMENTS

| | | | |
|---|---|---|---|
| 2,664,394 A | * | 12/1953 | Reeves ..................... 204/155 |
| 4,084,010 A | | 4/1978 | Takemoto et al. |
| 4,338,169 A | * | 7/1982 | Bienvenu ................. 75/10.67 |
| 5,433,965 A | | 7/1995 | Fischer et al. |
| 2003/0165603 A1 | | 9/2003 | Burklow et al. |
| 2004/0022913 A1 | | 2/2004 | Watson et al. |
| 2007/0059422 A1 | | 3/2007 | Robbins |
| 2007/0077339 A1 | | 4/2007 | Robbins |
| 2007/0082105 A1 | | 4/2007 | Robbins |

OTHER PUBLICATIONS

Paul Hancock and Brian J. Skinner. "oceanic density and pressure." The Oxford Companion to the Earth. Oxford University Press. 2000. Encyclopedia.com. Dec. 20, 2009 <http://www.encyclopedia.com>.*

* cited by examiner

Primary Examiner—Jennifer A Leung
(74) Attorney, Agent, or Firm—Malloy & Malloy, P.A.

(57) ABSTRACT

A baric electromagnetic thermal system for manufacturing disaccharide sweetener compounds is provided and permits baric and thermal processing, at low temperatures, to effect the retrocycloaddition, chemoselective promiscuous ligation, and cycloaddition reactions. A method for selecting base and adjunct components for the manufacture of a disaccharide sweetener compound having an equivalent functionality as a natural sweetener and/or derivative thereof as required for a specific food processing application is presented.

10 Claims, 4 Drawing Sheets

SYSTEM FOR PRODUCING CHEMICAL COMPOUNDS VIA A BARIC ELECTROMAGNETIC THERMAL PROCESS

CLAIM OF PRIORITY

The present application is based on and a claim to priority is made under 35 U.S.C. Section 119(e) to provisional patent application currently pending in the U.S. Patent and Trademark Office having Ser. No. 60/716,803 and a filing date of Sep. 13, 2005.

The present application incorporates by reference in its entirety Applicant's currently pending U.S. patent application Ser. No. 11/473,526 and a filing date of Jun. 23, 2006, and the present application also incorporates by reference in their entirety both of Applicant's U.S. patent applications contemporaneously filed on Sep. 13, 2006 with the U.S. Patent and Trademark Office, and having Ser. Nos. 11/520,483 and 11/520,484.

FIELD OF THE INVENTION

The present invention is directed to a novel baric electromagnetic thermal system for producing compounds, such as, in at least one embodiment, sweetener compounds. For example, in a preferred embodiment, the present invention is directed to a system for manufacturing a novel disaccharide sweetener compound, which is nutritive, natural, low-calorie, low-glycemic, and thermogenic so as to be fully functional for personal consumption as well as for use in the food and beverage industry. The novel baric electromagnetic thermal system permits the formation of unique compounds at relatively low temperatures without the need for metallic or other catalytic materials, or enzymes to initiate the reaction mechanisms. Moreover, the system of the present invention is structured to permit rapid and substantial pressure to be introduced into a processing vessel.

DESCRIPTION OF THE RELATED ART

Approximately 150 million persons in the United States use sugar-free low-calorie products, with their use having tripled over the last 20 years. It has been estimated that the consumption of both nutritive and non-nutritive sweeteners will increase about 3% per year over the next few years, with the market value of food additives inclusive of artificial sweeteners accounting for over $1.5 billion in the United States. All of the currently approved "high-intensity" sweeteners in the United States are synthetic substances. In addition, current pathos regarding the ubiquitous nature of sucrose and consumption by the populace (especially by children) is changing from relative apathy to a growing frenzy around the kitchen table. This growing move from ambivalence to activism dictates a new paradigm in sugar/sugar-option inclusion in and on food and in marketing.

To date, there are about 80 sweet compounds exclusive of monosaccharides, disaccharides, and polyols obtained from natural sources, with all of these from vascular plants. These plant-derived compounds mainly belong to three major structural classes, namely, the terpenoids, flavonoids, and proteins. At present, none of these highly sweet compounds (as individual, stand-alone sweeteners) have submitted self-affirmed GRAS status for use as a "high-intensity" sweetener in the United States, although plant-derived compounds such as glycyrrhizin, neohesperidin dihydrochalcone, stevioside, and thaumatin are used commercially in some other countries for sweetening purposes. However, in the United States there is an increasing use of plant extractives known to contain highly sweet terpenoids. Products comprising such extractives often use a "natural fruit flavors" declaration in the ingredient panel to comply with the 21CFR label declaration. An ammoniated derivative of the oleanane-type triterpene glycoside, glycyrrhizin, has been available for several years on the generally recognized as safe (GRAS) list of approved natural flavors. More recently, purified extracts of *Stevia rebaudiana* (Bertoni) Bertoni (Compositae) containing the sweet ent-kaurane-type diterpene glycosides stevioside and rebaudioside A have become popular as "dietary supplements." Steviosides cannot be declared as a food or food ingredient under 21CFR, but rather as a supplement in a supplement facts panel. Soft drinks incorporating extracts of *Siraitia grosvenorii* (Swingle) Lu & Zhang (Cucurbitaceae) fruits, also known as "Lo Han Kuo," containing sweet cucurbitane-type triterpene glycosides, such as mogroside V, are now on the market.

Sweetness is one of only four taste sensations we experience, and as such, sweeteners have been used in food and drink since man first began to prepare foods for consumption. For centuries, natural sweeteners such as honey and maple syrup, as well as those extracted from sugar cane and sugar beets have been utilized to enhance the foods we eat and the beverages we drink. Each of these natural sweeteners consists primarily of sucrose, a disaccharide comprised of the simple sugars, fructose and glucose. Glucose is, of course, an essential source of fuel for the body, so much so that the body produces glucose as part of our normal metabolic processes. In addition to providing the sweet taste we desire in many food and beverage products, natural sugars act as preservatives, such as in jams and jellies, they aid in the fermentation of breads, pickles, and alcoholic beverages, and they provide body and texture to baked goods and ice creams. Furthermore, these natural sugars are very stable compounds, even at significantly elevated temperatures, which make them highly desirable ingredients for the food industry. As a result, a wide variety of concentrated sources of natural sugars are commonly employed in the food industry, such as corn syrup, high fructose corn syrup, maltose, as well as a variety of sugar alcohols.

One drawback of these natural sweeteners is that they are typically high in caloric content, which is undesirable in today's health and weight conscious society, where counting calories has grown from a casual pass time to an obsession. Additionally, it has long been known that excess glucose, while essential in proper amounts for maintenance of a healthy body, is stored in the body as glycogens, which may be subsequently converted into unwanted fat. More importantly, elevated levels of glucose in the bloodstream can cause a hyperglycemic reaction in any of the numerous individuals afflicted with diabetes. The elevation in glucose levels in the bloodstream is not only a function of the amount of natural sweeteners, or other carbohydrates a person consumes, it is also a function of the rate at which these compounds are metabolized by the body. Fructose is approximately one and one half times sweeter than glucose, however, alone it does not possess other properties required to be fully functional as an alterative to natural table sugar, or sucrose.

One attempt to overcome the shortcomings of natural table sugar, i.e., reduction or elimination of the glucose component, includes blending a natural fruit sugar such as, by way of example, fructose, with a polysaccharide as a substitute for the glucose component of natural table sugar. Regardless of how vigorous the blending process, the resultant composition remains a non-homogenous blend which presents significant problems in handling and application, due to settling and layering of the components over time, as well as uneven distribution of the natural monosaccharide with the polysaccharide component. More specifically, it is not possible through blending to achieve and maintain a one to one distribution of each monosaccharide molecule and a corresponding one of the monosaccharide constituents of the polysaccharide, as there is no chemical bonding between the components.

Further attempts to address the foregoing shortcomings of natural sweeteners have led to the development of a number of chemical sweeteners, many in just the last century. Among the first of these chemical sweeteners to enjoy widespread commercial usage were sodium salts of cyclohexanesulfamic acid, more commonly known as cyclamates. Cyclamates are generally about 40 to 60 times as sweet as natural sweeteners, however, they contain essentially no calories or nutritional value. Although cyclamates have long since been banned in the United States as a potential cancer causing agent, they are still utilized elsewhere around the world, including Canada.

Saccharin is another chemical sweetener being about 300 times as sweet as sucrose, or natural sugar. As with cyclamates, saccharin contributes essentially no calories and no nutritional value to the food or beverage products in which they are utilized. Although studies have linked saccharin to bladder cancer in rats, public opposition led to a moratorium on a ban to its use in the United States, however, products containing saccharin must carry a warning label as a potential health hazard. Another non-nutritional chemical sweetener in use today is acesulfame K which is approximately 200 times as sweet as sucrose and is chemically similar to saccharin.

One further chemical sweetener on the market today is aspartame which, like acesulfame K, is about 200 times as sweet as sugar. Although aspartame contains the same caloric content of proteins, being formed of amino acids, due to the small volume required relative to natural sweeteners, the contribution to the overall caloric intake is minimal. One of the amino acids from which aspartame is formed, phenylalanine, may be harmful to phenylketonuric children, and thus, products containing aspartame must carry warning labels to that effect.

As these chemical sweeteners range from about forty to several hundred times sweeter than sucrose, or other natural sweeteners, only a small relative amount is required to achieve the same level of sweetening for a particular food or beverage product. This, of course, presents a significant problem in recipes that utilize a natural sweetener simply due to the reduced volume and relative ratio of ingredients to be used. In addition, chemical sweeteners do not react the same as natural sweeteners when cooking, baking, or otherwise processing a food product, regardless of the fact that some may be heat stable at somewhat elevated temperatures. As one example, due to the reduced volume of the sweetener added, many products baked with chemical sweeteners are typically denser and provide a smaller yield. Also, natural sweeteners act as a preservative, as noted above, however, chemical sweeteners do not impart preservative properties resulting in either a shorter shelf life of the products, or the addition of further, potentially harmful, chemical preservatives. Yet another negative aspect of chemical sweeteners is that foods baked with natural sweeteners have a natural brown coloration due to caramelization of the natural sweetener, however, this appealing aesthetic is lacking in goods baked with chemical sweeteners. Of course, the most common complaint about all chemical sweeteners known to date is that they simply do not taste the same, i.e. do not taste as good, as natural sweeteners.

Thus, it would be beneficial to provide a sweetener compound providing the benefits of a natural sweetener while minimizing or eliminating the undesirable effects. For example, it would be beneficial to provide a sweetener compound which is derived from naturally occurring components, such as a simple natural sugar and a polysaccharide, to produce a disaccharide which is functionally similar to sucrose, but is low-caloric and low glycemic. In addition, any such disaccharide sweetener compound should possess equivalent functional properties as their wholly natural counterparts such that direct substitution into any of a plurality of known food processing operations may be effected. It would also be helpful to provide such a disaccharide sweetener compound that is low-glycemic and metabolizes slowly upon ingestion. A further benefit may be realized by providing a disaccharide sweetener compound containing any of number of vitamins, minerals, and/or other fortifiers, which may be delivered to the digestive system without negatively impacting the sweetness index of the overall compound. A process for manufacturing such a disaccharide sweetener compound utilizing known chemical processing equipment would be preferable. It would also be beneficial to provide a method of selecting a natural sugar and an adjunct component from which to manufacture a disaccharide sweetener compound that emulates the functionality of one or more natural sweeteners utilized in a food processing operation, based upon user specific sweetener applications.

Traditional methods of manufacturing compounds, such as the chemical sweeteners mentioned above, can involve various processes. Among the more common processes are thermal processes, which involve manipulation of heat, and baric processes, which involve manipulation of pressure. In many instances, thermal and baric processes are combined in the production of compounds. These processes typically require high temperatures in order to induce separation or formation of chemical bonds between and among the various components used to produce the compounds. Moreover, such processes typically involve catalysts or enzymes to initiate the reaction mechanisms for separating or combining components into the desired compounds. However, the complexity and expense of using high temperatures and catalysts or enzymes in the manufacturing of compounds can hinder commercial viability of compounds produced in such a way. Furthermore, such processes do not provide for manipulation of the electromagnetic properties of the components.

Thus, it would therefore be beneficial to provide a system for manufacturing compounds that permits the formation of unique compounds at relatively low temperatures without the need for metallic or other catalytic materials, or enzymes to initiate the reaction mechanisms. Moreover, it would be helpful to provide a system structured to permit rapid and substantial pressurization of a process vessel. Further, it would be beneficial for such a system to permit control of baric, electromagnetic and thermal parameters as to enable non-catalytic cycloaddition and/or retrocycloaddition. It would also be preferable for such a system to permit control of baric, electromagnetic and thermal parameters so as to enable chemoselective ligation, cross-linking or cross-bonding, and entrainment of the components being processed therein. It would be additionally beneficial to provide a system which permits operation in semi-batch or continuous mode so as to permit increased throughput.

SUMMARY OF THE INVENTION

The present invention is directed to a novel baric electromagnetic thermal system for manufacturing compounds. The baric electromagnetic thermal system permits the formation of unique compounds at relatively low temperatures without the need for metallic or other catalytic materials, or enzymes to initiate the reaction mechanisms. Moreover, the system of the present invention is structured to permit rapid or substantial high pressurization of a processing vessel. In at least one embodiment, the present invention is directed to a system for manufacturing a novel disaccharide sweetener compound.

As one example, a disaccharide sweetener compound may be manufactured with the present system via a process of cracking a polysaccharide, for example, a glycoside, into its constituent monosaccharide molecules under elevated pressures in a processing vessel, known as retrocycloaddition. In the process of cracking the polysaccharide, hydrogen and oxygen are released from the polysaccharide as well. Next, a base component, for example, a naturally occurring fruit sugar such as fructose or galactose, may be introduced into the processing vessel with the constituent monosaccharide molecules derived from the polysaccharide, and the components are heated at reduced pressure to induce chemoselective promiscuous ligation of the constituent monosaccharide molecules with the base monosaccharide molecules. Finally, a rapid and substantial high pressure is introduced into the processing vessel resulting in cycloaddition of the base monosaccharide with a constituent monosaccharide derived from the polysaccharide. The cycloaddition process results in the release of one hydrogen molecule from the base component, which joins the hydrogen and oxygen released from the polysaccharide to from a water byproduct. Subsequent addition of fortifiers such as vitamins and minerals may be accomplished via baric processing to effect cross-linking or cross-bonding with the disaccharide. In some embodiments, an electromagnetic source polarizes the molecular structure of the components, thereby enhancing the baric and thermal process mechanisms.

A process for manufacturing such novel disaccharide sweetener compounds is provided to allow the various baric, electromagnetic, and thermal processing steps outlined above to be performed, at relatively low temperatures. In at least one embodiment, the process further includes a first stage processing vessel into which base and adjunct components, as well as any fortifiers which may be desired, are initially charged and separated via vacuum induction of the vessel, and a plurality of screens of varied mesh sizes to effect the separation prior to charging a second stage processing vessel with each component, as needed.

A method for selecting base and adjunct components for the manufacture of a disaccharide sweetener compound having an equivalent functionality as a natural sweetener and/or derivative thereof as required for a specific food processing application is also presented.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

The present invention is directed to a novel baric electromagnetic thermal system for producing compounds, generally shown as 10 throughout the Figures. In at least one embodiment, the present invention is directed to a system for manufacturing a novel disaccharide sweetener compound.

As discussed in more detail below, system 10 of the present invention permits the formation of unique compounds at relatively low temperatures without the need for metallic or other catalytic materials, or enzymes to initiate the reaction mechanisms. The present invention further permits rapid and substantial high pressure to be introduced into a processing vessel, as discussed in further detail below.

Also discussed herein, system 10 of the present invention permits control of baric, electromagnetic and thermal parameters to enable selective non-catalytic cycloaddition and/or retrocycloaddition, chemoselective ligation, cross-linking or cross-bonding, and entrainment.

Figure 1:
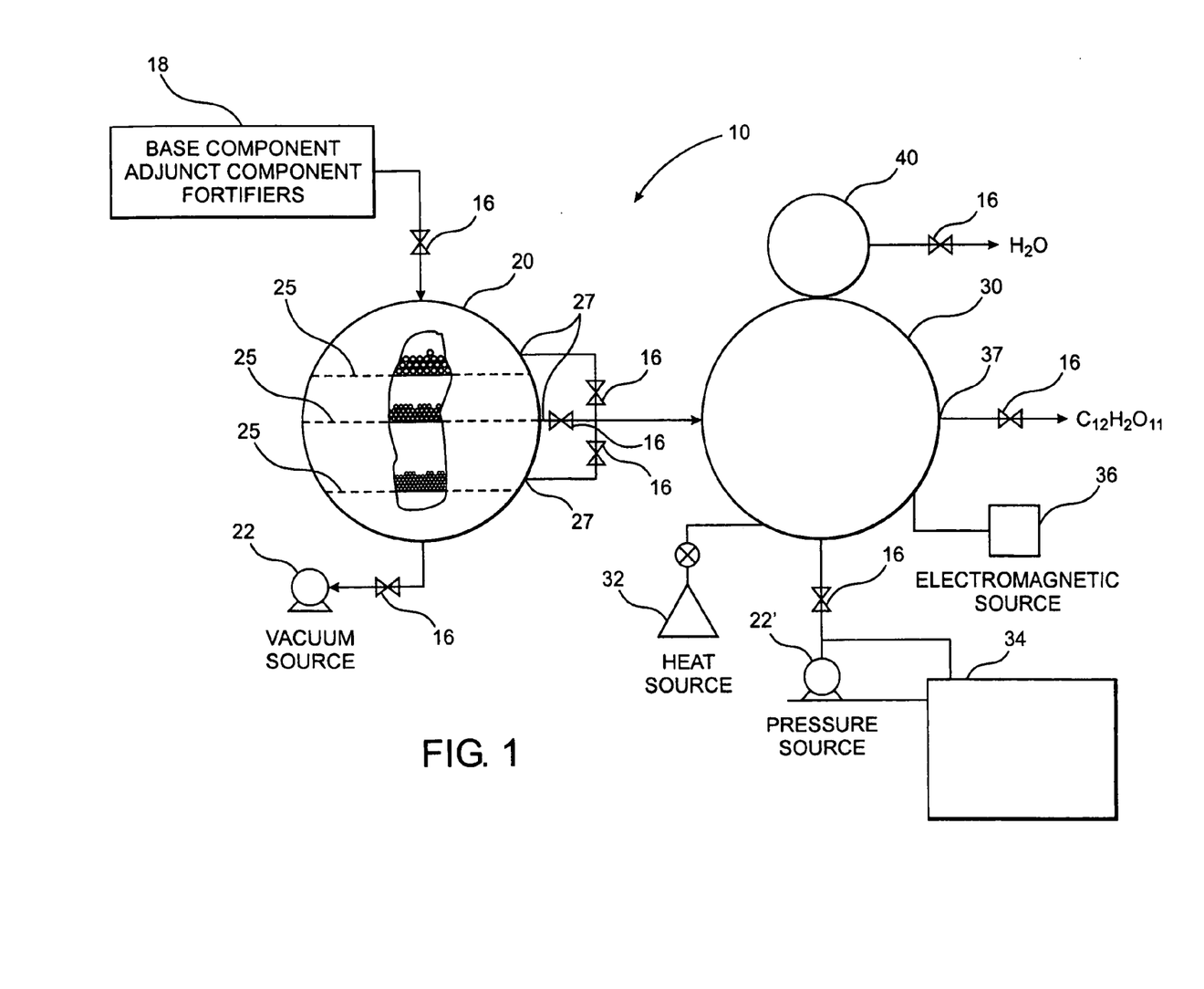
FIG. 1 is a schematic diagram of a baric electromagnetic thermal system for manufacturing compounds in accordance with the present invention.

Referring now to FIG. 1, the novel baric electromagnetic thermal system for producing compounds in accordance with the present invention, is generally indicated as 10. In at least one embodiment, the system 10 comprises a hopper 18 structured to temporarily contain at least one component, for example, a polysaccharide component. In one other embodiment, hopper 18 is structured to temporarily contain a monosaccharide component, a polysaccharide component, and one or more vitamins or other fortifiers. Hopper 18 is disposed in a material communicating relation with a first stage processing vessel 20 and structured to permit charging of a predetermined amount of at least one component into the first stage processing vessel 20. The charging occurs as a result of a pressure gradient between hopper 18 and first stage processing vessel 20 such that the at least one component moves from the hopper 18 to the first stage processing vessel 20. In at least one embodiment, a control valve 16 is employed between the hopper 18 and the first stage processing vessel 20 which is structured to regulate an amount of the at least one component charged into the first stage processing vessel 20.

The first stage processing vessel 20, in at least one embodiment, is utilized to separate and store the components for delivery to and further processing in a second stage processing vessel 30, which is disposed in a material communicating relation with first stage processing vessel 20 and structured to receive the at least one component from the first stage processing vessel 20.

In one embodiment, the first stage processing vessel 20 comprises a series of screens 25 of various mesh sizes structured to effect the separation of the components based upon the physical size of each component such that only components of a predetermined size may pass through a given mesh size. In addition, the first stage processing vessel 20 may be charged through an upper portion to allow gravity to facilitate the separation of the components through the vertically spaced apart screens 25. In one further embodiment, the first stage processing vessel 20 is structured to operate under a vacuum so as to further facilitate the physical separation of the components into their respective fractions.

To facilitate the separation of the components in the first stage processing vessel 20, vacuum source 22 is disposed in a baric communicating relation with the first stage processing vessel 20 and structured to permit adjustment of a first stage pressure within the first stage processing vessel 20. In at least one embodiment, a vacuum is applied to a lower portion of the first stage processing vessel 20. In at least one embodiment utilized for small scale production, the vacuum source 22 comprises a three-stage, 150 horsepower turbo-molecular positive-negative displacement vacuum motor with entrapment, backstreaming, and outgassing management capability.

Material communication between first stage processing vessel 20 and second stage processing vessel 30 is achieved via a pressure gradient sufficient to induce the transfer of a preselected component from first stage processing vessel 20 to second stage processing vessel 30. The pressure gradient is achieved by lowering the pressure in second stage processing vessel 30 below the pressure in the first stage processing vessel 20.

In at least one embodiment, both the first stage and second stage processing vessels 20 and 30 are structured to be operable over considerable and rapid pressure changes, and as such, at least one embodiment comprises processing vessels having a spherical configuration so as to permit equal pressures to be rapidly and evenly achieved throughout the entire vessel. The present invention may comprise commercially available and existing or retrofitted processing vessels having alternate geometric configurations including, but not limited to, conical, ovoid, or elongated cylindrical, just to name a few. The rapid pressure changes which may be effected in a spherical processing vessel, however, results in an increase in the throughput of the process of the present invention.

In addition, first stage processing vessel 20 comprises one or more discharge conduits and/or discharge ports 27 disposed in a material communicating relation with second stage processing vessel 30 and are structured to transfer each component on an as needed basis into the second stage processing vessel 30. In at least one embodiment, control valves 16 are used to control the transfer of each component into the second stage processing vessel 30.

A heat source 32 is disposed in a thermal communicating relation with second stage processing vessel 30 and is structured to permit adjustment and control of a temperature within second stage processing vessel 30. In at least one embodiment, heat source 32 comprises a heated and water cooled jacket. By way of example, heat source 32 is structured to permit adjustment and control of temperatures within a processing vessel, e.g., the second stage processing vessel 30, within a range of 85 to 115 degrees Fahrenheit.

In a preferred embodiment, pressure source 34 is disposed in a baric communicating relation with at least second stage processing vessel 30, and the pressure source 34 is structured to permit a rapid, mostly instantaneous, and significant change in pressure within the second stage processing vessel 30. In at least one embodiment, pressure source 34 comprises at least one but preferably a plurality of entrapment, backstreaming and outgassing condensation tanks disposed in series. For example, in at least one embodiment used for small scale production, pressure source 34 comprises a 150 gallon condenser/evaporator tank.

Pressure source 34 is further structured to induce rapid pressurization of second stage processing vessel 30. In at least one embodiment, pressure source 34 is pressurized to a substantially high pressure. Thereafter, the opening of a control valve 16 permits rapid pressurization of second stage processing vessel 30. In at least one embodiment of the present invention, rapid pressurization of second stage processing vessel 30 can occur on the order of one second. For example, second stage processing vessel 30 can be rapidly subjected to pressure in the range of about two to five thousand feet below sea level in a period of one-half to two seconds.

Figure 3:
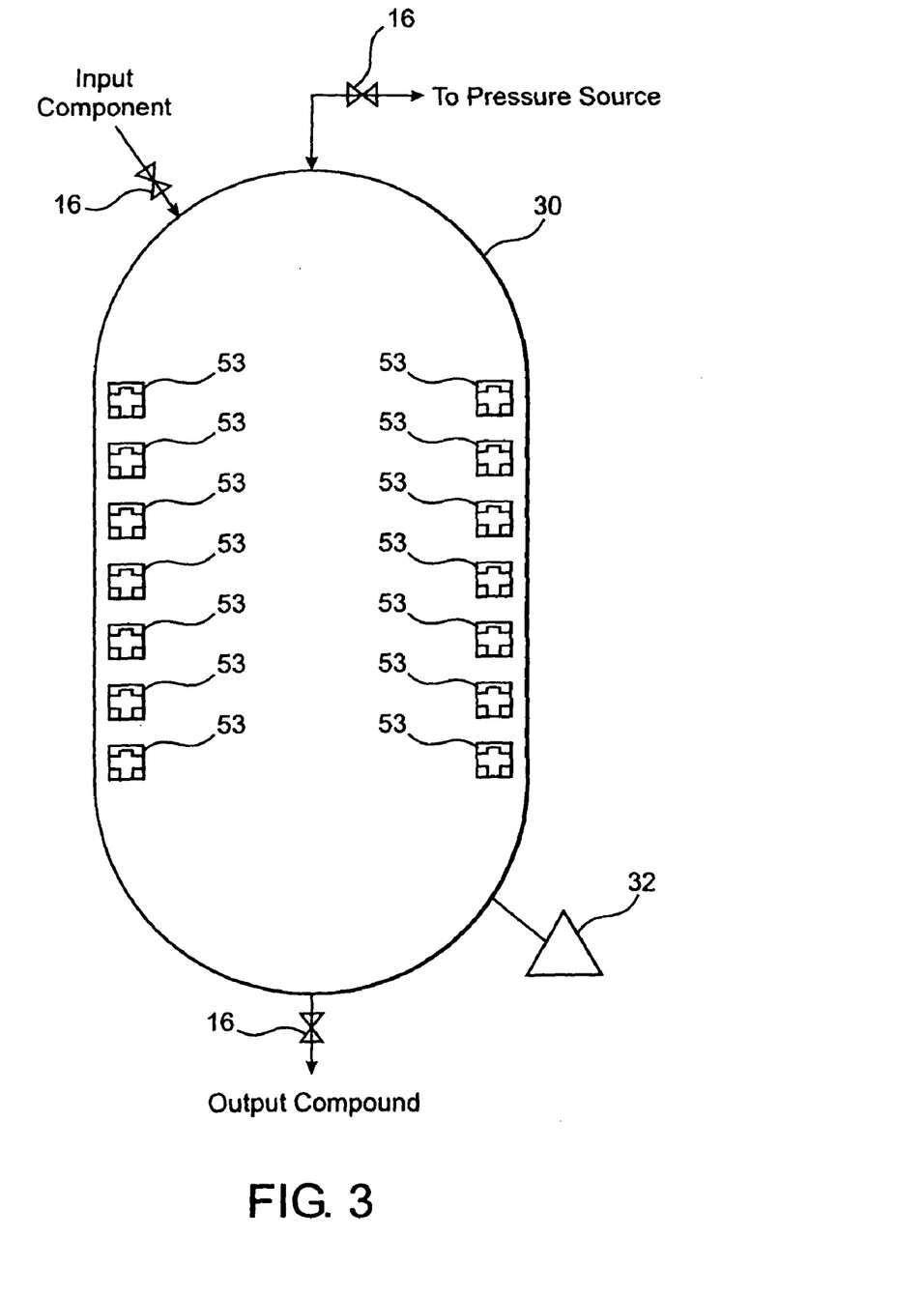
FIG. 3 is a schematic diagram of a baric electromagnetic thermal system for manufacturing compounds, comprising bipolar electromagnets in accordance with the present invention.

In a preferred embodiment, an electromagnetic source 36 is disposed in an electromagnetic communicating relation with second stage processing vessel 30 and structured to permit adjustment of an electromagnetic field within second stage processing vessel 30. For example, FIG. 3 shows at least one embodiment of electromagnetic source 36 comprising a plurality of bipolar alternating field electromagnets 53 disposed in a vertically spaced, oppositely disposed, parallel relation along a vertical axis within second stage processing vessel 30, each set of electromagnets being oppositely disposed 180 degrees about the vertical axis so as to face one another. Specifically in the illustrative embodiment of FIG. 3, fourteen bipolar alternating field electromagnets, comprising seven oppositely disposed pairs, are biased by 0.5 volt positive to negative to generate an alternating electromagnetic field from 0.5 gauss to 20,000 gauss. The parallel alignment of the electromagnets polarizes the molecular structure of the components exposed to the electromagnetic field within the second stage processing vessel, thereby enhancing the baric and thermal process mechanisms. For example, in a preferred embodiment of the present invention, the electromagnetic process induces polarization of the electrons in the valence ring of a target component, such as mogroside molecules and fructose molecules. The formula for determining the mass of a vessel is $M=3/2(PV)d/5$.

A stereo metric chamber 40 is disposed in a material communicating relation with the second stage processing vessel 30 and is structured to receive process byproducts, such as water, from the second stage processing vessel 30. In at least one embodiment, stereo metric chamber 40 is structured to permit measurement of water production and stoichiometry, in a process for producing a disaccharide or polysaccharide compound.

In at least one embodiment, second stage processing vessel 30 comprises a plurality of screens 25 of various mesh sizes structured to effect the separation of the target compound produced and one or more process byproducts based upon the physical size of each such that only compounds of a predetermined size may pass through a given mesh size.

Second stage processing vessel 30 further comprises at least one discharge port 37 structured to discharge the target compound produced, such as, for example, disaccharide or polysaccharide sweetener compounds. In at least one preferred embodiment, discharge port 37 is located at or near the bottom of second stage processing vessel 30 such that gravity aids in the collection and discharge of the target compound produced.

In at least one other preferred embodiment, the first stage processing vessel 20 may be eliminated and the at least one component may be charged separately and directly into at least one processing vessel 30'. While this alternative embodiment is within the scope and intent of the present invention, a two stage processing arrangement is preferred for several reasons. First, the use of a first stage processing vessel 20 in the manner described herein allows for the components to be stored and readied for transfer to the second stage processing vessel 30 at the required pressure, thereby eliminating the need to control pressure in a plurality of vessels and or transfer lines to charge the second stage processing vessel 30.

Further, and more importantly, the use of a two stage processing arrangement allows for continuous feed processing, versus single batch processing when just a single processing vessel is utilized, once again, significantly increasing throughput when utilizing the process of the present invention.

Figure 2:
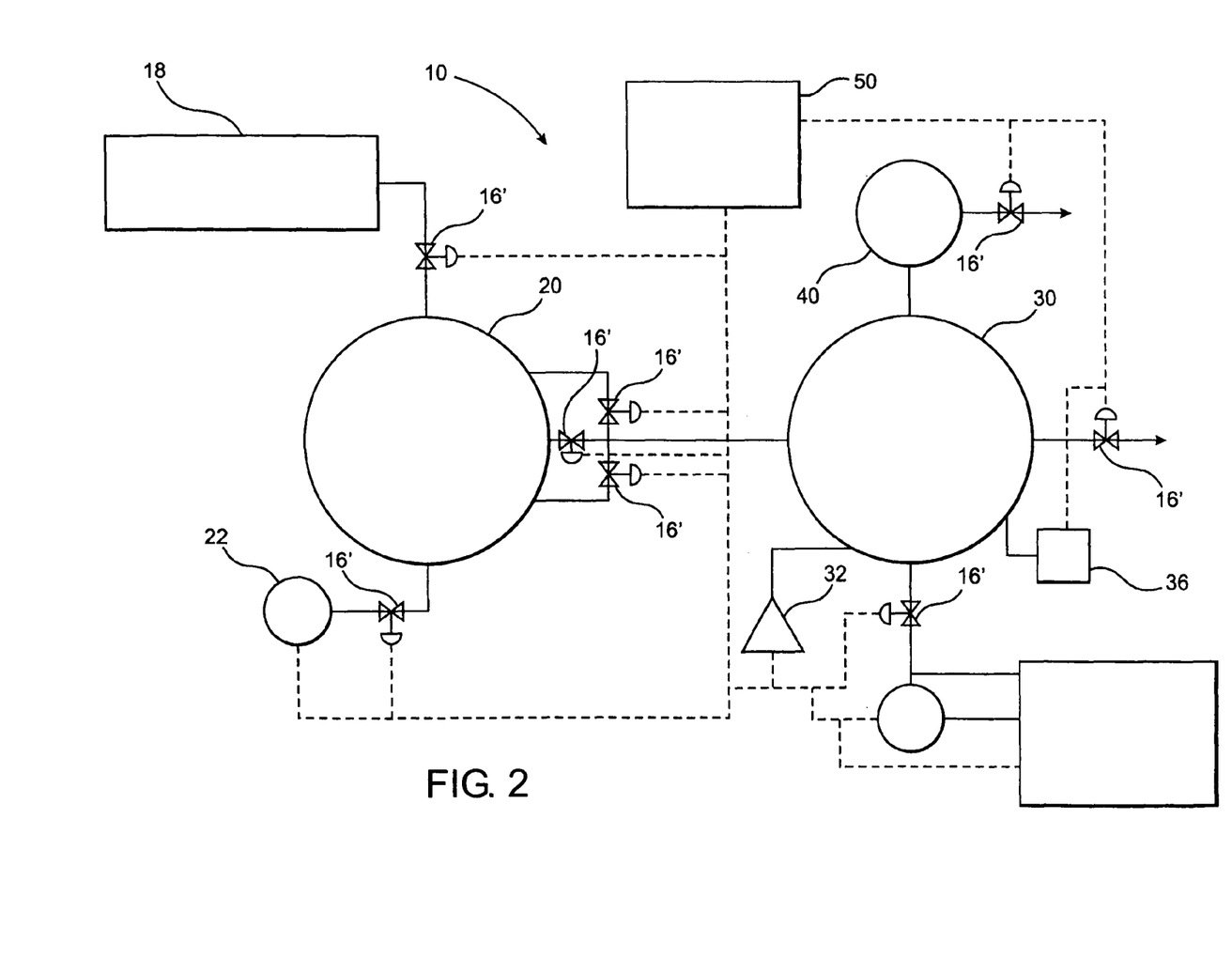
FIG. 2 is a schematic diagram of a baric electromagnetic thermal system for manufacturing compounds, comprising a control processor in accordance with the present invention.

Referring now to FIG. 2, at least one embodiment of the present invention is directed to a system 10 having a control processor 50. In accordance with at least one embodiment of the present invention, control processor 50 comprises a laptop computer. In at least one other embodiment, control processor 50 comprises a mainframe computer. The control processor enables automated or semi-automated operation of system 10 of the present invention.

In at least one embodiment, control processor 50 is disposed in a monitoring relation with first stage processing vessel 20 and structured to control the pressure within first stage processing vessel 20. More in particular, control processor 50 of the present invention is disposed in a communicating relation with vacuum source 22 and structured to control vacuum source 22. Control processor 50 is additionally disposed in a monitoring relation with second stage processing vessel 30 and structured to control the temperature and pressure within second stage processing vessel 30. Specifically, in a preferred embodiment, control processor 50 is disposed in a communicating relation with heat source 32 and structured to control at least the magnitude of heat generated by heat source 32. Control processor 50 is further disposed in a communicating relation with pressure source 34 and structured to control an available pressure within pressure source 34. In various embodiments, control processor 50 is disposed in a communicating relation with valves 16' and structured to control at least the opening and closing of valves 16'. In various embodiments, control processor 50 is also disposed in a communicating relation with electromagnetic source 36 and structured to control at least the magnitude of the electromagnetic field produced by electromagnetic source 36.

Looking now to one preferred embodiment of the compounds produced by the present invention, the disaccharide sweetener compounds produced by the present invention comprise at least one naturally occurring monosaccharide such as, by way of example, fructose, or another naturally occurring fruit sugar, in combination with a preselected polysaccharide including, but not limited to, naturally occurring glycosides such as curcurbitane, labdane, ent-kaurene, cycloartane, oleanane, secodammarane, and dammarane. In at least one embodiment, the glycoside may comprise mogroside IV or mogroside V. It is noteworthy that the novel disaccharide sweetener compounds of the present invention are not merely blends of the foregoing components, rather, they are unique compounds formed by chemoselective ligation and promiscuous bonding between a naturally occurring monosaccharide and the monosaccharide constituents that comprise a naturally occurring polysaccharide, as will be discussed more fully below.

As such, the novel disaccharide sweetener compounds of the present invention provide a homogeneous composition having the desired sweetening index, by virtue of the natural fruit sugar, without the undesirable effects of glucose by virtue of utilizing the monosaccharide constituents of a naturally occurring polysaccharide to form a new and novel disaccharide molecule from naturally occurring components. More in particular, as the invention is a new, novel and homogenous compound, it does not comprise the handling and processing problems associated with mere blends of a monosaccharide and a polysaccharide, as described above. Further, the particular combination of natural fruit sugar and polysaccharide may be preselected to produce a novel disaccharide sweetener compound that is functionally equivalent to any combination of natural sweeteners and/or derivatives thereof as may be required for personal consumption and/or commercial food processing operations. Further, the disaccharide sweetener compound of the present invention is digested longer and slower than sucrose or other saccharides without the expected laxative effect of polyols or other saccharide compounds, but is fully digested in the small intestine.

Several plant-derived compounds of the terpenoid and phenolic types may have commercial use as sweeteners, ligated sugars and/or sugar-options in the food and beverage industry. The present invention is directed toward the practical application of terpenoid and phenolic compounds through novel techniques of reducing or fractionating, the aforementioned glycosides, i.e., mogroside IV and/or mogroside V, into fractions and the conjugation of those fractions via promiscuous ligation to a base carbohydrate, such as a naturally occurring sugar, thereby forming a novel disaccharide sweetener compound from the bound constituents. Glycosides, as used in the present invention, are defined as any organic compounds that yield a sugar and one or more non-sugar substances on hydrolysis. In the case of some plant-derived compounds, these are further expressed as either hydrolysable or non-hydrolysable.

The novel disaccharide compound of the present invention comprises a fX, where f=fraction and X=the size or number of glycoside fractions, for example, mogroside fractions, in their resulting pentose or hexose configurations of glycoside/mogroside linked to a hexose and/or pentose which, in one preferred embodiment, comprises fructose. The hexose/pentose constituent of the molecule, once again, for example, fructose, provides initial sensory sweetness by binding to the sugar receptors on the tongue and the fX provides the intensity of sensory sweetness, while the nature of the disaccharide linkage or the nature of the modification prevents the glycoside from being metabolized in the same manner as sucrose. The intensity or sweetness of the resulting disaccharide is determined by fX, as the length of the prime fraction determines how deep within the sweet receptors the sugar penetrates and, thus, lengthens the amount of time the receptors are stimulated or that more points of reception and/or interaction are stimulated. It should be noted that in the mogroside IV and V fractions, the fX has at least four known points of potential ligand and interaction with host carbohydrates or other polar moieties. These points of potential reception are found at the C-1, C-2, C-4 and C-5 hydroxyl and carbon groups with the C-4-β-OH hydroxyl and C-1 carbon offering the best points of linkage. In a preferred embodiment, one (1) host carbohydrate is linked (α-1(C-1 carbonyl group)-O-β-2) to the smallest possible fraction of a mogroside, i.e., α-1-O-β-2 linked α-D-(momo)mogropyranosol, β-D-fructofuranose, producing a sweetener that is in relative terms, 1.017:1 times as sweet as sucrose.

A number of sweet-tasting, plant-derived terpenoids and phenolics and other naturally occurring glycosides have been isolated and characterized, including the bisabolane sesquiterpenoids, hernandulcin and 4β-hydroxyhernandulcin, cucurbitane, the labdane diterpene glycoside—gaudichaudioside A, the oleanane triterpenoid glycoside—periandrin V, the cycloartane triterpene glycosides—abrusosides A-E, the 3,4-seco-dammarane triterpene glycosides—pterocaryosides A and B, the semisynthetic dihydroflavonol—dihydroquercetin 3-acetate (4'-methyl ether), and the proanthocyanidin—selligueain A. One preferred embodiment of the present invention, as noted above, comprises mogroside(s) IV and/or V derived from *Momordica Grosvenori*, also known as Lo Han Guo. The mogrosides IV and V have been selected for cracking or fractioning via the process of the present invention for two primary reasons: 1) the supply chain is already established and the mogrosides IV and V are readily available in sufficient quantities to produce commercially required amounts of the novel disaccharide sweetener compound; and, 2) they are known to be safe and efficacious. Further, upon cracking or fractioning, these mogroside fractions are about 250 to 300 times as sweet as sucrose.

Looking now to the process of manufacturing a novel disaccharide sweetener compound in accordance with the present invention, a base component, specifically, a naturally occurring monosaccharide is selected, such as fructose, or another natural fruit sugar, to be the backbone, if you will, of the novel disaccharide sweetener compound. In at least one embodiment, the base component selected is a ketohexose sugar such as, D-fructose, D-sorbose, D-psicose, or D-tagatose. Next, an adjunct component comprising a suitable naturally occurring polysaccharide compound is selected based upon user specific application requirements, which may be simply a substitute for natural table sugar thus comprising the same functionality of sucrose, or it may be a specific combination of natural sugars and/or derivatives thereof which is utilized in a commercial food processing environment. In a broad sense, the functionality includes such factors as comparable density, pourability, and thermogenic properties of the target composition, just to name a few. In some cases, the palatability, or mouth feel, of the target composition may be of importance, for example, when the target composition is utilized for direct personal application to a food or beverage for consumption, such as table sugars, honey, and syrups, just to name a few.

In at least one embodiment, one half of the disaccharide comprises the single smallest fraction, $f_x$ [where $f_x \Phi = r_1 \ldots r_N \div \psi$, and ab initio calculations of $\psi$ are determined by $F(1)$ $\Phi_c \cdot (1) \epsilon_1 \Phi_1 (1)$ and the limit, $\Lambda$, of $\Psi$ are determined by computational input], of a mogroside that has been reduced or decomposed from its original molecular structure via a non-metallic, non-enzymatic baric-thermal cycloelimination reaction of process of the present invention, with the resultant components being individual cyclohexose and cyclopentose saccharide molecules that are the non-glucose element of the disaccharide sweetener compound of the present invention. The extraneous result of the present process induces water activity and the loss of nitrogen when present in the mogroside structure. These individual cyclohexose components do not establish valence or linkage with other similar cyclohexose molecules because the functional density field within the processing vessel, as described further below, inhibits bonding, keeping the molecules in a state on anti-bonding per $\Phi CF = ((a+kb)(1)(b+ka)(2) + (b+ka)(1)(a+kb)(2))((\alpha(1)\beta(2) - \beta(1)\alpha(2))$.

Looking now to the process associated with system 10 of the present invention, a first stage processing vessel 20 is charged with the appropriate amounts of each of the base component and the adjunct component, as illustrated schematically in FIG. 1. The first stage processing vessel 20 is utilized to separate the components for delivery to and further processing in a second stage processing vessel 30.

As indicated above, the first stage processing vessel 20 is utilized to separate and store the base and adjunct components for delivery to the second stage processing vessel 30. As such, the first stage processing vessel 20 comprises a series of screens 25 of various mesh sizes to effect the separation of the base and adjunct components based upon the physical size of each. As will be appreciated, the first stage processing vessel 20 is charged through an upper portion to allow gravity to effect the separation of the components through the screens 25. Additional screens 25 may be utilized to separate any of a variety of fortifiers which may be incorporated into the novel disaccharide sweetener compound including, but not limited to, vitamins, minerals, and/or other fortifiers as may be required for a specific application. To facilitate the separation of the components in the first stage processing vessel 20, a vacuum may be applied to a lower portion of the first stage processing vessel 20.

Once the first stage processing vessel 20 has been charged and placed under vacuum for a period of time, the base and adjunct components, and any fortifiers as may be required, will physically separate into layers within the first stage processing vessel 20. Next, an amount of the adjunct component, a preselected polysaccharide, is drawn into the second stage processing vessel 30, by lowering the pressure in the second stage processing vessel 30 to slightly below the pressure in the first stage processing vessel 20 to produce a pressure gradient sufficient to induce the transfer of the adjunct component from the first stage processing vessel 20 to the second stage processing vessel 30.

Once charged with the adjunct component, the pressure in the second stage processing vessel 30 is returned to ambient pressure, or approximately one (1) bar. Next, a low amount of heat is applied to the second stage processing vessel 30 just to the point where the bonds of the adjunct component begin to crack, and then the adjunct component is rapidly subjected to pressure in the range of about two to five thousand feet below sea level for a period of one-half to two seconds, after which, the pressure in the second stage processing vessel 30 is rapidly returned to ambient pressure, or about one (1) bar.

This thermal and baric processing of the adjunct component, previously known as retrocycloaddition, but more recently known and hereinafter referenced as cycloelimination, results in cleaving the individual monosaccharide constituents from each polysaccharide component, with the subsequent release of a hydrogen and oxygen atom for each monosaccharide molecule cleaved, without destroying the individual six chain carbon constituents. Due to the subsequent release of the hydrogen and oxygen atoms, the individual monosaccharide constituents do not bond or otherwise recombine with one another upon return to ambient pressure of approximately one (1) bar. To further assure against such recombination, the oxygen and hydrogen released from cracking of the adjunct component may be evacuated into a stereo metric chamber 40 above the second stage processing vessel 30.

Following thermal and baric processing of the adjunct component, which effectively cleaves the constituent monosaccharide molecules from the adjunct component, the second processing vessel 30 is charged with a stoichiometric amount of the base component. To effect the transfer of the base component from the first stage processing vessel 20 to the second stage processing vessel 30, a slight pressure gradient is again created between the two vessels by reducing the pressure in the second stage processing vessel 30, thereby creating a pressure gradient sufficient to effect a transfer of the required amount of the base component from the first stage processing vessel 20 to the second stage processing vessel 30.

After charging the second stage processing vessel 30 with the base component, the pressure in the second stage processing vessel 30 is reduced to pressure equivalent to about 29,000 feet above sea level, and the temperature in the second stage processing vessel 30 is elevated to between about 85 and 115 degrees Fahrenheit. By heating the components at a relatively low temperature, such that thermal decomposition does not occur, yet at a significantly reduced pressure, the base components and the monosaccharide constituents of the adjunct component are induced into a state of chemoselective promiscuous ligation with one another, but not with themselves. More in particular, chemoselective promiscuous ligation is at least partially defined by two asymmetrical and differentiated molecules reacting exclusively with one another rather than combining with each other, or reforming into the original long chain molecule from which they were derived.

While the base component and the monosaccharide constituents of the adjunct component are in the state of chemoselective promiscuous ligation, the pressure in the second stage processing vessel 30 is rapidly increased to a range equivalent to between about two and five thousand feet below sea level. This rapid pressure increase is effected in approximately one second and causes cycloaddition between one base component molecule and one molecule of the monosaccharide constituent of the adjunct component, the cycloaddition resulting in the release of a hydrogen atom from each base component molecule.

As such, the net result of the process is the production of one novel disaccharide sweetener compound for each base molecule, and the subsequent formation of one water molecule from the hydrogen released by each base component molecule during cycloaddition, and the hydrogen and oxygen molecule released for each monosaccharide constituent produced from the adjunct component during the thermal and baric cracking of the adjunct component. Further, via the present process, it is possible to obtain a high purity product, typically in the range of 90 to 100 percent of the disaccharide formed by this process is of a desired composition. In addition, the measure of water formation provides a means for measurement of the production of the novel disaccharide sweetener compound, as they are formed in a one to one molar ratio, as per the following simplified chemical equation of the aforementioned process:

$$nC_6H_{11}O_6 + n(C_6H_{11}O_5 + OH) \rightarrow nC_{12}H_{22}O_{11} + nH_2O$$

wherein $nC_6H_{11}O_6$ represents (n) moles of the base component, $n(C_6H_{11}O_5)$ represent (n) moles of the monosaccharide constituent of the adjunct component after thermal and baric processing, or cracking, and n(OH) represents (n) moles each of oxygen and hydrogen released from the adjunct component during cracking, resulting in $nC_{12}H_{22}O_{11}$ represents (n) moles of the novel disaccharide sweetener compound produced, along with (n) moles of water, a byproduct of the reaction process. A further feature of this novel process for manufacturing a disaccharide sweetener compound is that the water formed as a reaction byproduct is available to adjust the moisture content of the disaccharide sweetener compound which, depending on its ultimate application, may vary from a substantially dry composition to a slurry of the sweetener compound in water.

In at least one embodiment, one or more fortifiers may be added to the novel disaccharide sweetener compounds. One fortifier may comprise a vitamin, or an entire daily recommended dosage of vitamins for a specific group of person, for example, the daily recommended dosage of vitamins for children. Additionally, or alternatively, one or more mineral supplements may be combined with the novel disaccharide sweetener compound as a fortifier. Other compounds may be utilized as fortifiers, which are cross linked or cross bonded to disaccharide via further baric processing. Specifically, the disaccharide sweetener compound produced in accordance with the present invention is reduced to a pressure equivalent to about 20,000 feet above sea level in the second stage processing vessel 30. As a result of this hypobaric pressure, the disaccharide sweetener compound is induced into a relaxed, opened state due to the repulsive forces of magnetically opposite portions of the compound. As such, the compound is open to combine with of one or more fortifiers which are charged into the second stage processing vessel 30 from the first stage processing vessel 20. The combination of the fortifiers with the disaccharide sweetener compound of the present invention is via a cross linking or cross bonding mechanisms, not by means of actual covalent bonding between these components. Additionally, and as noted above, one or more fortifiers or other constituents may be entrained within the physical structure of the disaccharide sweetener compound of the present invention once it returns to a normal, closed state. After the fortifier(s) have been charged to the second stage processing vessel 30, the pressure in the second stage is returned to approximately ambient pressure, allowing the disaccharide sweetener compound to return to a closed configuration, thereby entrapping the fortifier within.

Figure 4:
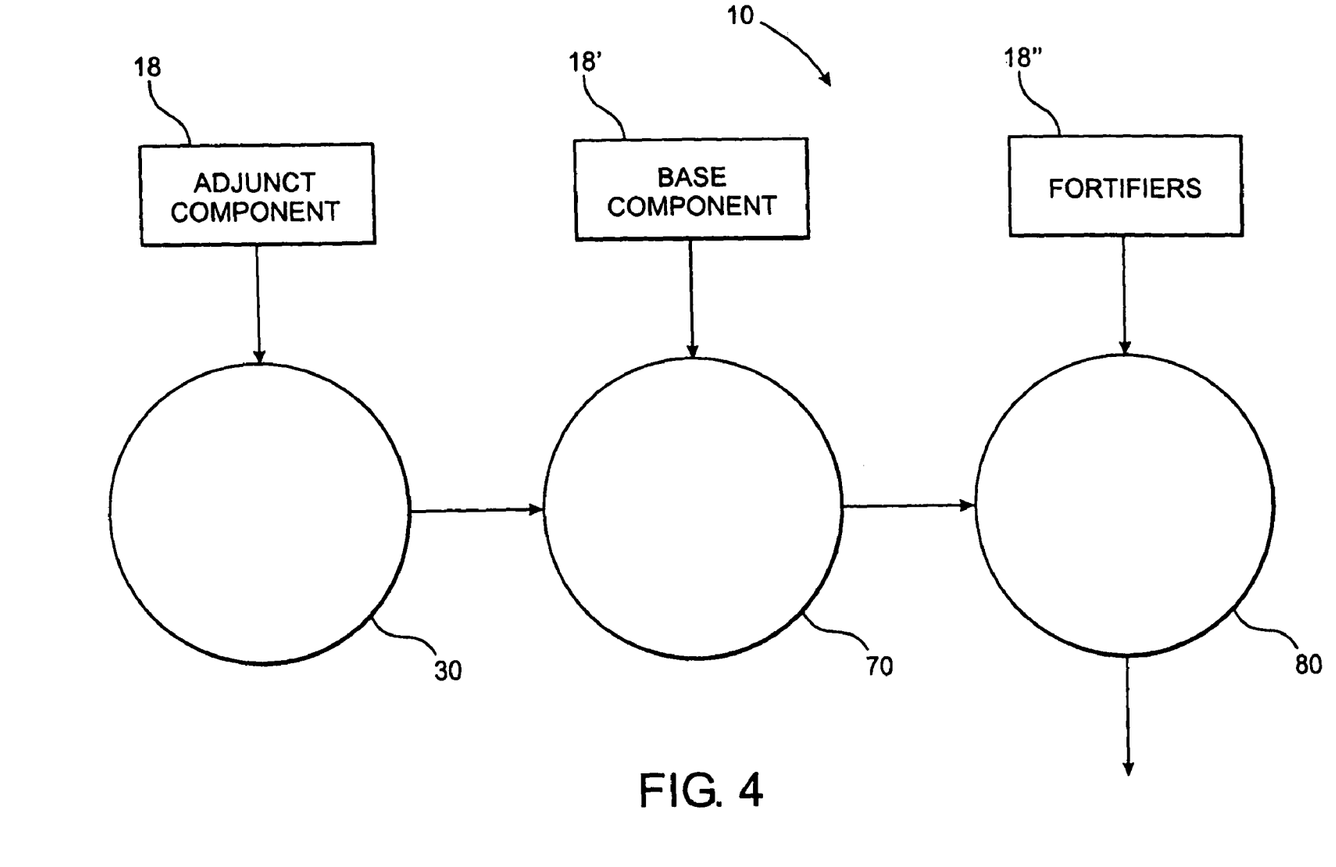
FIG. 4 is a schematic diagram of a baric electromagnetic thermal system for manufacturing compounds, comprising a plurality of processing vessels in accordance with the present invention.

With reference to FIG. 4, at least one embodiment of the system 10 of the present invention comprises a plurality of processing vessels. While the embodiment depicted in FIG. 1 may be preferable for certain embodiments, such as small scale production, a plurality of processing vessels benefits at least some larger, commercial production embodiments of the present invention. Specifically, the embodiment as depicted in FIG. 4 permits a continuous, or at least semi-batch, mode of operation.

In at least one embodiment, system 10 comprises a plurality of processing vessels, such as, by way of example only, a second stage processing vessel 30, a third stage processing vessel 70, and a fourth stage processing vessel 80. In at least one embodiment, third stage processing vessel 70 and fourth stage processing vessel 80 comprise substantially similar configurations to second stage processing vessel 30, as described above. While various embodiments include one or more first stage processing vessels 20, in at least one embodiment, the first stage processing vessel 20 is eliminated and one or more components are charged directly into one or more processing vessels. For example, in the illustrative embodiment of FIG. 4, a preselected amount of an adjunct component may be transferred separately and directly into a second stage processing vessel 30, a preselected amount of a base component may be transferred separately and directly into a third stage processing vessel 70, and a preselected amount of a fortifier may be transferred separately and directly into a fourth stage processing vessel 80.

As discussed briefly above, in at least one embodiment, the process may be performed in a plurality of processing vessels. By way of example, with respect to the above described process for manufacturing a disaccharide sweetener compound, an adjunct component is charged directly into second stage processing vessel 30 from hopper 18. Once charged with the adjunct component, the pressure in the second stage processing vessel 30 is returned to ambient pressure, or approximately one (1) bar. Next, a low amount of heat is applied to the second stage processing vessel 30 just to the point where the bonds of the adjunct component begin to crack, and then the adjunct component is rapidly subjected to pressure in the range of about two to five thousand feet below sea level for a period of one-half to two seconds, after which, the pressure in the second stage processing vessel 30 is rapidly returned to ambient pressure, or about one (1) bar, causing cycloelimination.

Following cycloelimination of the adjunct component, the cycloeliminated adjunct components are transferred from second stage processing vessel 30 into third stage processing vessel 70. Additionally, a base component is charged directly into third stage processing vessel 70 from hopper 18'. After charging the third stage processing vessel 70 with the base component, the pressure in the third stage processing vessel 70 is reduced to pressure equivalent to about 29,000 feet above sea level, and the temperature in the third stage processing vessel 70 is elevated to between about 85 and 115 degrees Fahrenheit. By heating the components at a relatively low temperature, such that thermal decomposition does not occur, yet at a significantly reduced pressure, the base components and the monosaccharide constituents of the adjunct component are induced into a state of chemoselective promiscuous ligation with one another, but not with themselves. While the base component and the monosaccharide constituents of the adjunct component are in the state of chemoselective promiscuous ligation, the pressure in the third stage processing vessel 70 is rapidly increased to a range equivalent to between about two to five thousand feet below sea level. This rapid pressure increase is effected in approximately one second and causes cycloaddition between one base component molecule and one molecule of the monosaccharide constituent of the adjunct component, the cycloaddition resulting in the release of a hydrogen atom from each base component molecule. As such, the net result of the process is the production of one novel disaccharide sweetener compound for each base molecule plus the byproducts discussed above.

Following cycloaddition, the novel disaccharide sweetener compound is transferred from third stage processing vessel 70 into fourth stage processing vessel 80. Additionally, a fortifier is charged directly into fourth stage processing vessel 80 from hopper 18". Thereafter, the pressure in fourth stage processing vessel 80 is reduced to a pressure equivalent to about 20,000 feet above sea level in the fourth stage processing vessel 80. As a result of this hypobaric pressure, the disaccharide sweetener compound is induced into a relaxed, opened state due to the repulsive forces of magnetically opposite portions of the compound. The combination of the fortifiers with the disaccharide sweetener compound of the present invention is via a cross linking or cross bonding mechanisms, not by means of actual covalent bonding between these components. Additionally, and as noted above, one or more fortifier or other constituent may be entrained within the physical structure of the disaccharide sweetener compound of the present invention once it returns to a normal, closed state. The pressure in the second stage is then returned to approximately ambient pressure, allowing the disaccharide sweetener compound to return to a closed configuration, thereby entrapping the fortifier within.

The present invention further comprises a method of selecting components for a disaccharide sweetener compound specifically for use in a preselected food processing application, as noted above. As such, the present invention allows for the manufacture of novel disaccharide sweetener compounds which emulate a natural sweetener and/or derivatives thereof for use in any of a plurality of food processing applications. More specifically, the present invention provides a novel disaccharide sweetener having an equivalent functionality as a natural sweetener or natural sweetener derivative, wherein the functionality includes such factors as comparable density, pourability, and thermogenic properties, just to name a few. In some cases, as noted above, the palatability, or mouth feel, of the disaccharide sweetener compound may be of importance, for example, particularly when the compound is to be utilized for direct personal application and consumption in a food or beverage, such as table sugars, honey, and syrups, just to name a few.

The method comprises analysis of the composition to be replaced with a novel disaccharide sweetener compound which may include, but is by no means limited to, measurement of the Brix, or sweetness index of the composition, as well as other physical properties such as density, viscosity, particle size distribution. In addition, infrared spectroscopy and/or thermal signature imaging may be utilized to further characterize the composition to be replaced. Based upon these parameters, an appropriate combination of base component and adjunct component may be selected for manufacture of a disaccharide sweetener compound having an equivalent functionality.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:
1. A baric electromagnetic thermal system for producing compounds, comprising:
   a first stage processing vessel structured to temporarily contain at least one preselected component;
   a vacuum source disposed in a baric communicating relation with said first stage processing vessel and structured to permit adjustment of a first stage pressure within said first stage processing vessel;
   a second stage processing vessel disposed in material communication with said first stage processing vessel and structured to receive said at least one preselected component from said first stage processing vessel;
   said second stage processing vessel further structured to retain said at least one component therein during at least one preselected processing step of said at least one preselected component;
   a heat source disposed in a thermal communicating relation with said second stage processing vessel and structured to permit adjustment of a second stage temperature within said second stage processing vessel;
   a pressure source disposed in a baric communicating relation with said second stage processing vessel and structured to permit adjustment of a second stage pressure within said second stage processing vessel;
   said pressure source further structured to permit adjustment of said second stage pressure within said second stage processing vessel within generally about one-half to two seconds;
   a control processor disposed in a communicating relation with said first stage processing vessel and structured to control said first stage pressure within said first stage processing vessel;
   said control processor further disposed in a communicating relation with said second stage processing vessel and further structured to control said second stage pressure within said second stage processing vessel; and
   said control processor disposed in a communicating relation with said second stage processing vessel further structured to control said second stage temperature within said second stage processing vessel.
2. The system as recited in claim 1 wherein said first stage processing vessel further comprises at least one screen structured to separate said at least one preselected component.

3. The system as recited in claim 2 wherein said at least one screen comprises a mesh structured to allow a material of predetermined size to pass through.

4. The system as recited in claim 1 further comprising a hopper structured to temporarily contain said at least one preselected component, wherein said hopper is disposed in a material communicating relation with said first stage processing vessel and further structured to charge said first stage processing vessel with said at least one preselected component.

5. The system as recited in claim 1 wherein said first stage processing vessel further comprises at least one discharge port disposed in a material communicating relation with said second stage processing vessel and structured to discharge said at least one preselected component into said second stage processing vessel.

6. The system as recited in claim 1 further comprising a stereometric chamber disposed in a material communicating relation with said second stage processing vessel and structured to receive process byproducts from said second stage processing vessel.

7. The system as recited in claim 1 wherein said second stage processing vessel further comprises at least one discharge port structured to discharge said compounds.

8. The system as recited in claim 1 wherein said control processor is disposed in a communicating relation with said vacuum source and structured to control said vacuum source.

9. The system as recited in claim 1 wherein said control processor is disposed in a communicating relation with said heat source and structured to control said heat source.

10. The system as recited in claim 1 wherein said control processor is disposed in a communicating relation with said pressure source and structured to control said pressure source.

* * * * *